UNITED STATES PATENT

[19] Perry et al.
[11] 4,434,650
[45] Mar. 6, 1984

[54] HYDROCARBON SENSOR FLOAT

[75] Inventors: Ralph A. Perry, Indianapolis; Raymond J. Andrejasich, Carmel, both of Ind.

[73] Assignee: Emhart Industries, Inc., Indianapolis, Ind.

[21] Appl. No.: 374,999

[22] Filed: May 5, 1982

[51] Int. Cl.³ .................................. G01N 25/18
[52] U.S. Cl. ......................... 73/61.1 R; 340/603; 441/29
[58] Field of Search ............... 73/61.1 R, 322.5; 374/156; 441/29, 28, 21; 340/631, 627, 603, 604

[56] References Cited

U.S. PATENT DOCUMENTS

| 3,698,025 | 10/1972 | Worobel | 441/28 X |
| 4,048,854 | 9/1977 | Herzl | 73/61.1 R X |
| 4,220,041 | 9/1980 | Potter | 73/61.1 R |
| 4,221,125 | 9/1980 | Oliver et al. | 73/61.1 R |
| 4,345,459 | 8/1982 | Perry et al. | 73/61.1 R |

FOREIGN PATENT DOCUMENTS

| 211422 | 10/1957 | Australia | 73/322.5 |
| 460100 | 5/1928 | Fed. Rep. of Germany | 374/156 |
| 2305783 | 9/1974 | Fed. Rep. of Germany | 441/28 |
| 2601410 | 7/1977 | Fed. Rep. of Germany | 73/61.1 R |
| 270178 | 5/1927 | United Kingdom | 374/156 |
| 2050955 | 1/1981 | United Kingdom | 441/21 |

Primary Examiner—Gerald Goldberg
Assistant Examiner—Tom Noland
Attorney, Agent, or Firm—Robert F. Meyer

[57] ABSTRACT

A hydrocarbon sensor float for use in detecting the presence of hydrocarbons on the surface of a liquid provides an elongated floatation member having a top end and a bottom end and also having a cavity located centrally therealong and extending completely therethrough, a sensor assembly including a sensor and at least one electrical conductor coupled to the sensor, the sensor assembly being positioned in said floatation member for locating the sensor in the cavity for allowing access of the liquid thereto and for causing the electrical conductor to extend from the top end of the floatation member, and an attachment for a variable amount of weight at the bottom end of the floatation member for providing a variable floatation level for the member with respect to the liquid surface and likewise for the sensor for allowing adjustment of the detection depth for hydrocarbons at an installation site.

6 Claims, 2 Drawing Figures

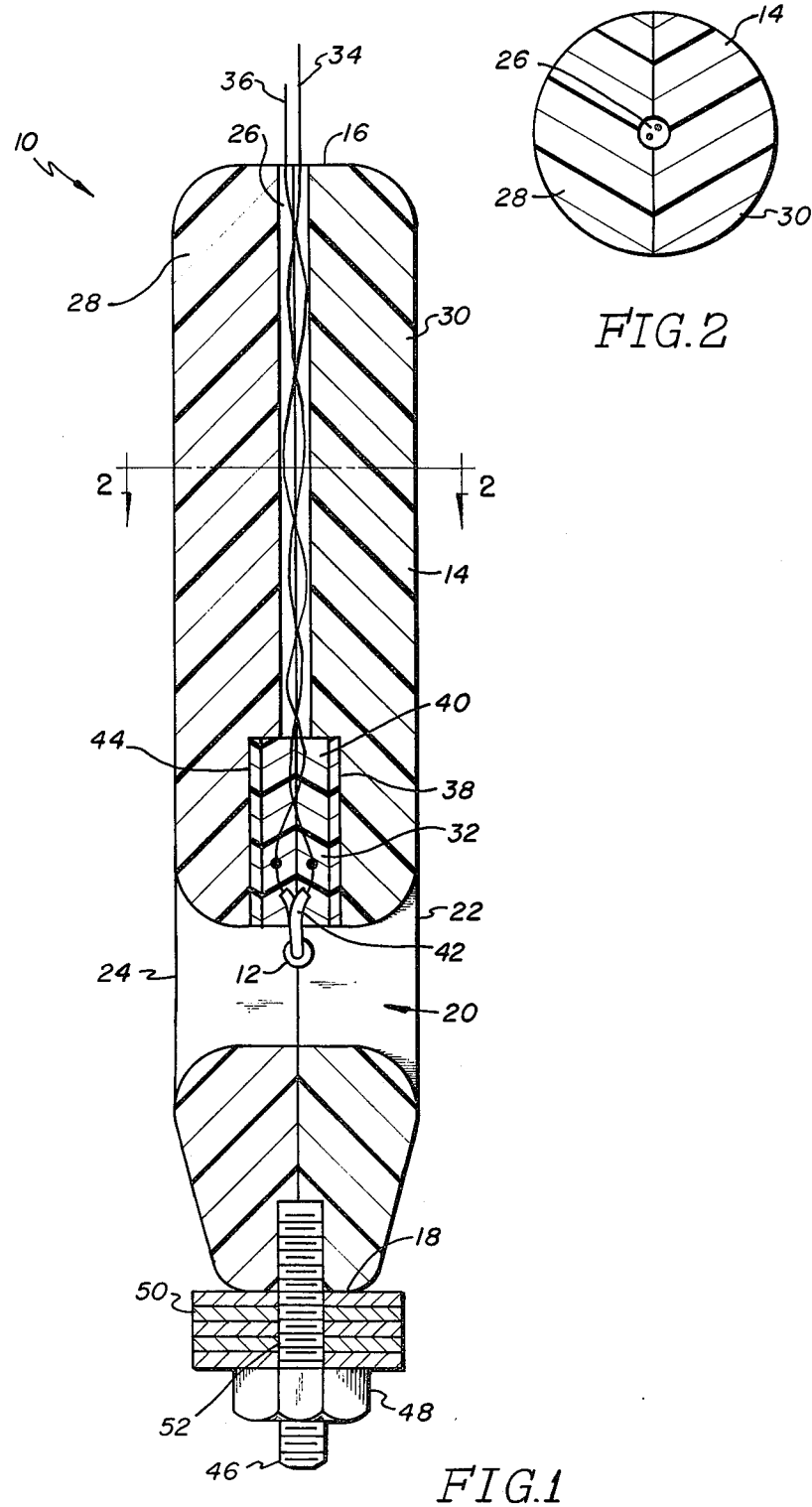

HYDROCARBON SENSOR FLOAT

BACKGROUND OF THE DISCLOSURE

1. Field of The Invention

The present invention generally relates to sensor floats and, in particular, to sensor floats for use in the detection of hydrocarbons.

2. Statement of The Prior Art

Instruments and sensors for the detection of underground hydrocarbon contamination have become increasingly popular over recent years due to increased awareness of such environmental pollution. For this reason, various forms of sensors and sensing instruments have been developed. Several of the sensors developed have been intended for use at the surface of a body of water such as oceans, lakes, and in underground wells at the ground water level. Various instruments and sensors for this purpose are described in U.S. Pat. Nos. 4,221,125 to John Oliver, et al and 4,286,208 to George French, et al and also in current pending U.S. patent applications Ser. No. 197,953 filed Oct. 17, 1980 by Ralph Perry (now U.S. Pat. No. 4,384,477), Ser. No. 197,955 filed Oct. 17, 1980 by Ralph Perry and Raymond Andrejasich (now U.S. Pat No. 4,361,031) and Ser. No. 198,058, filed Oct. 17, 1980 by Ralph Perry and James Booe (now U.S. Pat. No. 4,345,459). The instruments described therein have proven useful and reliable in a large variety of installations. Generally, the floats which support the sensors as described in the latter three references above, are installed into 4" diameter wells or larger which are drilled to below the water level. Thusly, the sensor floats float on the water level and can detect hydrocarbon substances thereat. Also as described in the latter three references, the instruments and floats are designed to sense hydrocarbon liquids at a variety of depths or thicknesses on the water's surface. Unfortunately, the full application of such instruments and sensors throughout all of the industries which use hydrocarbon fluids has not yet been realized. Thus, any improvements which would make the present instruments and sensors more readily adaptable to existing hydrocarbon fluid installations would correspondingly increase the rate of installation of such systems and thereby improve control of hydrocarbon fluid pollution.

SUMMARY OF THE INVENTION

Accordingly, a sensor float has been developed which is useable for detecting various thicknesses of hydrocarbon substances and also useable in already existing 2" diameter test wells which are readily available throughout the hydrocarbon industries. A hydrocarbon sensor float for use in detecting of the presence of hydrocarbons on the surface of a liquid, comprises an elongated floatation member having a top end and a bottom end, the elongated member having a cavity means located centrally therealong and extending completely therethrough, a sensor assembly including a sensor and at least one electrical conductor coupled to the sensor, means for positioning the sensor assembly in the floatation member for locating the sensor in the cavity means, for allowing access of the liquid thereto, and for causing the electrical conductor to extend from the top end of the floatation member, and means for attaching a variable amount of weight to the bottom end of the floatation member for providing a variable floatation level for the member with respect to the liquid surface and likewise for the sensor for allowing adjustment of the detection depth for hydrocarbons at an installation site.

BRIEF DESCRIPTION OF THE DRAWINGS

The present invention is illustratively described in respect to the accompanying drawings in which:

FIG. 1 is a cross-sectional view of a sensor float constructed in accordance with one embodiment of the present invention; and FIG. 2 is a sectional view of the device of FIG. 1 taken along view lines 2—2.

DETAILED DESCRIPTION OF THE DRAWINGS

FIG. 1 generally shows a sensor float 10 on which is mounted a hydrocarbon liquid sensor 12. The float 10 generally includes a float member 14 which may be constructed from any suitable floatation material, which in the present case is a polyurethane foam. The float member 14 has a generally elongated shape with a top end 16 and a bottom end 18. As shown in FIG. 2, the floatation member 14 has a cylindrical cross section. The floatation member 14 also has a cavity 20 formed therein along the elongated portion thereof. The cavity 20 extends through floatation member 14 from one side 22 to the other 24. The float member 14 further includes a centrally located longitudinal passageway 26 extending from the top end 16 to the cavity 20. Further, the float member 14 is constructed from two identical halves 28 and 30, both of which extend from the top end 16 to the bottom end 18. Identical as they are, they have in common the cavity 20 and the passageway 26. Thusly formed, the passageway 26 is concentrically located with respect to the cylindrical shape of the floatation member 14 and may itself be cylindrical in shape.

The sensor 12 is part of a sensor assembly 32 which further includes at least one electrical conductor 34 and in the present case a second electrical conductor 36. Any suitable sensor 12 may be used for the present invention. In the present embodiment, the sensor 12 is a semiconductor which is a diode. However, the specific sensor used is not essential and different sensors, such as transistors, may be used with the present invention. Also, future sensors may be developed which only require a single electrical conductor 34, and such sensors would be useable with the float of the present invention.

The sensor assembly 32 further includes a cylindrical shaft 38 which is filled with a potting material in the area 40. The potting material serves to seal the interconnection between the sensor 12 and the electrical conductors 34 and 36 from the detrimental effects of environmental exposure. Any suitable electrically insulating potting material may be used. The sensor 12 which is used is a diode made by Unitrode and designated UR 710. To prevent electrical shorting of the diode's terminals by ground water and other detrimental environmental effects, the sensor 12 is encapsulated in a polyolefin shrink tubing which is further protected by being impregnated with a polyimide or polyamide sold by the Amoco Chemical Company and designated AI 830. Impregnation of the tubing is accomplished by vacuum impregnation for approximately five minutes and then baking the combination to further harden the polyimide, As shown in FIG. 1, the shrink tubing 42 extends within the cylinder 38 to accomplish sealing thereof from the environment by the potting material. Further in the present embodiment, the cylindrical section 38 is formed from a chemically inert epoxy-fiberglas combination which is commonly available and which is sandblasted on the inside surface to promote adherence of the potting material thereto.

The sensor assembly 32 is mounted or positioned by means of an enlargement 44 in the central passageway 26 for locating the sensor in the cavity, for allowing access of liquid thereto, and for causing the electrical conductors 34 and 36 to extend through the top end 16 of float member 14. The means 44 is simply a cylindrical enlargement of the passageway 26 which allows the halves 28 and 30 of float member 14 to capture the cylindrical section 36 during assembly of the float 10. The cylindrical section 38 may further be bonded to either or both halves 28 and 30 during assembly.

The sensor float 10 further includes means for attaching a variable amount of weight to the bottom end 18 of float member 14 for providing a variable floatation level for the float member 14 with respect to a liquid surface and likewise for the sensor for allowing adjustment of the detection depth for hydrocarbon fluids at an installation site. The means for attaching generally includes a threaded shaft 46 which is embedded in the bottom end 18 of float member 14 and extends downwardly therefrom. A nut 48 is engageable with the shaft 46 for the purpose of maintaining a plurality of weights 50 between the nut 48 and the bottom end 18. The weights 50 shown are generally annular in shape and include a central hole 52 therethrough for allowing engagement thereof by the shaft 46 and nut 48.

During installation of the sensor float 10, an installer may determine what amount or depth of hydrocarbon substances he or she wishes to detect. It may be that a test well already has hydrocarbon liquids in it, either at a constant known amount or just an occasional trace amount which the installer does not want to have setting off his detection instrument. In this case, the installer may increase the number of weights 50 affixed to the bottom end 18 and thereby lower the level of the float member and thus the sensor 12 to a given depth below the surface of the water in which the sensor float 10 will float. Thusly, the sensor 12 will extend below the hydrocarbon liquid level already existing and be exposed only to the water on which the hydrocarbon liquids are floating. As the amount of hydrocarbon liquids upon the ground water increases, the floatation level of the float and the sensor 12, with respect to the water/hydrocarbon interface, will rise causing the sensor to be exposed to the hydrocarbon liquids, and thusly cause an indication of an increase in the level of hydrocarbon liquids present.

The shape and size of the sensor float 10 further enables the float 10 to be installable in a wide variety of already existing wells. Hydrocarbon processing installations such as refineries and storage areas already have a large number of 2" test wells drilled. Also, many of these wells already include some amount of hydrocarbon liquid. Thusly, the present invention is capable of quick and easy installation in such sites while further allowing customizing of each individual float 10 to its own installation by variation of the floatation level thereof.

The above description of one embodiment of the present invention is intended to be taken in an illustrative and not a limiting sense. Various modifications and changes may be made to the embodiment by persons skilled in the art without departing from the scope of the present invention as defined in the appended claims.

What is claimed is:

1. A sensor float for use in detecting the presence of foreign substances in a liquid comprising:
   (a) an elongated floatation member having top and bottom ends, a cavity extending across said elongated member near said bottom end and opening to sides thereof to permit the passage of liquid therethrough, and a centrally disposed elongated passageway extending from said top end to said cavity, said passageway including an enlarged section exposed to said cavity,
   (b) a sensor carried in said cavity including insulation means electrically insulating same from said liquid, electrical conductors extending through said passageway, connecting means interconnecting said sensor to said electrical conductors within said enlarged portion, and electrically insulative material carried within said enlarged portion and sealing said connecting means from the environment, and
   (c) means for attaching a variable amount of weight to said bottom end of said floatation member.

2. A sensor float according to claim 1 wherein said sensor includes a diode.

3. A sensor float according to claim 1 wherein said electrically insulative material includes potting material.

4. A sensor float according to claim 1 wherein said insulation means includes a polyolefin shrink material encapsulating at least a portion of said sensor.

5. A sensor float according to claim 4 wherein said polyolefin shrink material is tubing and wherein said tubing is impregnated with a polyimide.

6. The float of claim 1, wherein said means for attaching includes a threaded shaft attached to and extending from said bottom end of said floatation member, a nut engageable with said threaded shaft and a plurality of weights each having a hole therethrough for engaging said shaft and nut.

* * * * *